(12) United States Patent
Wang et al.

(10) Patent No.: US 7,215,736 B1
(45) Date of Patent: May 8, 2007

(54) X-RAY MICRO-TOMOGRAPHY SYSTEM OPTIMIZED FOR HIGH RESOLUTION, THROUGHPUT, IMAGE QUALITY

(75) Inventors: Yuxin Wang, Arlington Heights, IL (US); Wenbing Yun, Walnut Creek, CA (US); David Dean Scott, Oakland, CA (US)

(73) Assignee: Xradia, Inc., Concord, CA (US)

( * ) Notice: Subject to any disclaimer, the term of this patent is extended or adjusted under 35 U.S.C. 154(b) by 0 days.

(21) Appl. No.: 11/072,635

(22) Filed: Mar. 4, 2005

Related U.S. Application Data

(60) Provisional application No. 60/550,758, filed on Mar. 5, 2004.

(51) Int. Cl.
*G01N 23/00* (2006.01)
(52) U.S. Cl. .......................... 378/25; 378/21

(58) Field of Classification Search ............ 378/21–27, 378/195, 177
See application file for complete search history.

(56) References Cited

U.S. PATENT DOCUMENTS

| | | | | |
|---|---|---|---|---|
| 6,104,776 A | * | 8/2000 | Oikawa ........................ | 378/22 |
| 7,099,432 B2 | * | 8/2006 | Ichihara et al. ................ | 378/25 |
| 2003/0068010 A1 | * | 4/2003 | Lentfer ......................... | 378/81 |

* cited by examiner

*Primary Examiner*—Edward J. Glick
*Assistant Examiner*—Hoon Song
(74) *Attorney, Agent, or Firm*—Houston Eliseeva LLP

(57) ABSTRACT

A projection x-ray imaging system that possibly utilizes a laboratory-based micro-focused x-ray source is disclosed. Techniques for optimizing the system for high quality, three dimensional image formation with tomographic imaging with the potential for high resolution and high throughput are described. It also concerns ways to optimize the system design to obtain improved image quality.

14 Claims, 7 Drawing Sheets

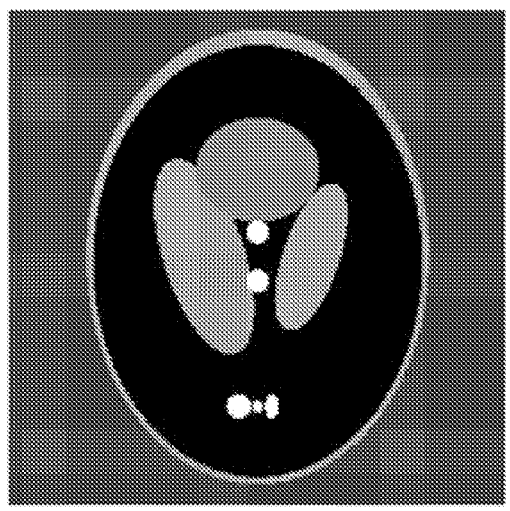
(a)
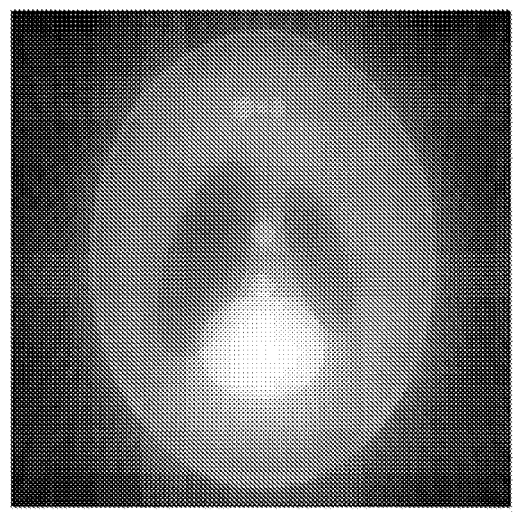
(b)
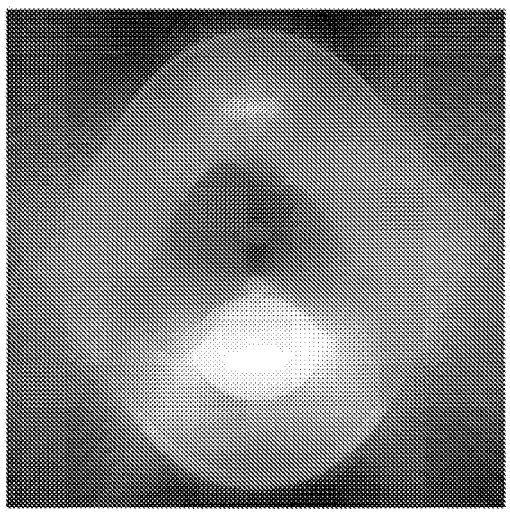
(c)
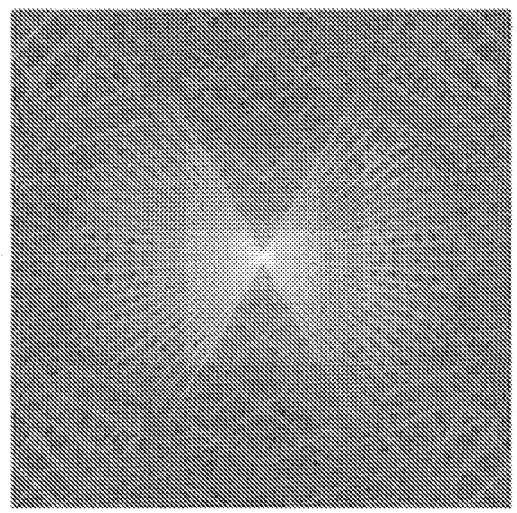
(d)
Fig. 5

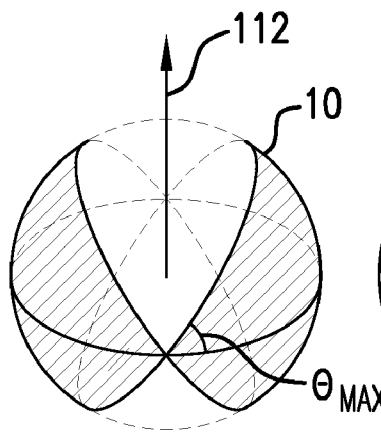 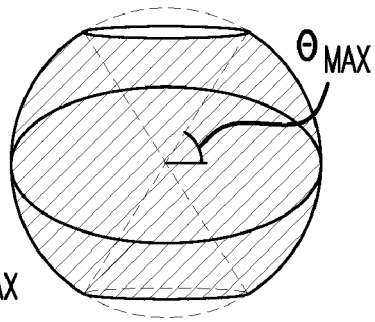 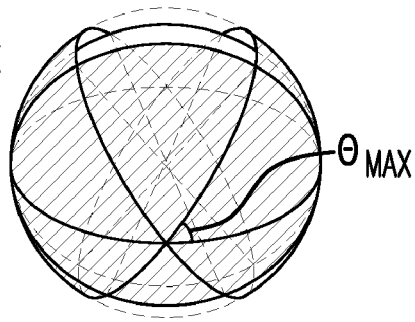
FIG.6A  FIG.6B  FIG.6C
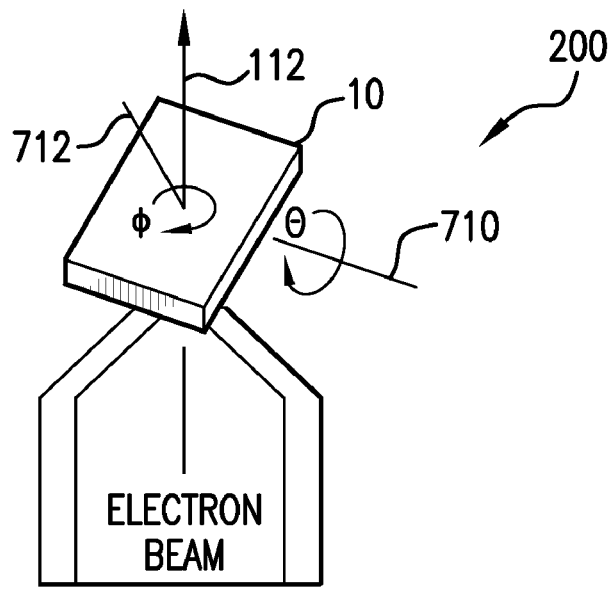
FIG.7

X-RAY MICRO-TOMOGRAPHY SYSTEM OPTIMIZED FOR HIGH RESOLUTION, THROUGHPUT, IMAGE QUALITY

RELATED APPLICATIONS

This application claims the benefit under 35USC 119(e) of U.S. Provisional Application No. 60/550,758, filed Mar. 5, 2004, which is incorporated herein by reference in its entirety.

BACKGROUND OF THE INVENTION

The ability of x rays to penetrate through material has been exploited extensively, such as in non-invasive and non-destructive imaging in medical and industrial applications.

For example, a number of manufacturers have developed imaging tools for failure analysis of integrated circuit (IC) packaging that take advantage of the penetrating power of hard x rays with tens to hundreds of kilo electron-Volts (keV) energy. These x-ray inspection tools typically provide resolutions on the order of tens of micrometers. This is sufficient for inspecting most large features in IC packages. They provide sample mounting mechanisms and multi-axis motion control to allow the operator to translate, zoom, and tilt the sample with a joystick while observing the image in real time are widely deployed in packaging failure analysis (FA) labs.

Often, these tools are arranged in a relatively simple projection geometry, in which the radiation produced by an x-ray source is allowed to penetrate the sample, and the transmitted radiation is collected by the detector. With this setup, the geometrical magnification of the system is:

$$M = \frac{L_s + L_d}{L_s}, \quad (1)$$

where, $L_s$ is the source to sample distance and the $L_d$ is the sample to detector distance. As a result, the achievable resolution of these systems can be derived, being roughly:

$$\delta \geq \frac{M-1}{M} s, \quad (2)$$

where s is the size of the x-ray source spot.

From this relationship, in order to achieve high resolution, one should make M as close to 1 as possible. In the limit where M=1, the sample plane overlaps the detector plane, which is the geometry for a contact printing mode.

Contact printing, however, requires a detector with high enough resolution to sample the contact, non-magnified image. Thus, the detector resolution must be on par with the sample features. Such high resolution detectors, however, tend to have low efficiencies, usually around 10% for x-ray energies above 100 keV.

In alternative imaging mode is to increase the geometric magnification so that the features in the sample are magnified sufficiently such that they can then be sampled with a detector with a more coarse resolution. The advantage is that these detectors tend to have much higher efficiencies.

In this projection mode, M>1, the resolution is often constrained to about the source size. Thus, high resolution requires a source with very small spot size, which tends to produce weaker x ray beams.

SUMMARY OF THE INVENTION

This invention pertains to a projection x-ray imaging system that possibly utilizes a laboratory-based micro-focused x-ray source. The invention concerns ways to optimize the system for high quality, three dimensional image formation with tomographic imaging with the potential for high resolution and high throughput. It also concerns ways to optimize the system design to obtain improved image quality.

In general, according to one aspect, the invention features a projection x ray imaging system. This system comprises an x ray source for generating an x ray beam and a sample motion stage. This stage rotates the sample in the x ray beam to enable tomographic data acquisition by enabling the generation of multiple projections for later tomographic reconstruction. A detector system is also provided for detecting the x ray beam after interaction with the sample.

In the present embodiment, the x ray source is a micro-focused x ray source. As such, the source or spot size is less then 50 micrometers and typically less than 5 micrometers, although it can be less than 2 micrometers or about 1 micrometer or less.

In the preferred embodiment, the sample motion stage comprises at least two rotation stages, one on the other. In one example, the sample motion stage comprises a θ stage having an axis of rotation that is perpendicular to the x ray beam and a φ stage that has an axis of rotation that is perpendicular to a plane of the sample. This enables the performance of conical tilt tomography data acquisition.

In the preferred embodiment, the distance between the sample and the source is relatively small in order to increase the photon flux in the sample. Preferably, the distance is between one and ten millimeters. In the preferred embodiment, the distance is less than two millimeters and even one millimeter or less.

In general, according to another aspect, the invention features a method to acquire tomographic data. This method comprises placing a sample in a beam of an x ray source to acquire projections at low tilt angles and then placing the sample at a greater distance from the x ray source to acquire projections at higher tilt angles.

In the present embodiment, the step of acquiring the projections at low tilt angles is performed at a distance between the sample and the source of less than ten millimeters. It is preferably two millimeters or less. The step of acquiring the projections at high tilt angles is provided at a larger distance between the sample and the source such as 10 to 50 millimeters.

In general, according to another aspect, the invention features a method for performing tomographic reconstruction. This method comprises acquiring projections of structures in a sample at a limited number of angles and then generating a tomographic image by using projections and information concerning the structures i.e., a priori knowledge. In one example, this a priori knowledge is that the structures are layered. Thus, the step of generating the tomographic image comprises forcing the values between the layers to be a background value. This can often be used for electronic components such as semiconductor integrated circuits, packaging, and circuit boards and other systems that are fabricated using multilayered lithography techniques.

In other examples, CAD design data are used to fill in the information.

In some embodiments, the step of generating the tomographic image comprises filling areas in Fourier space by interpolating using a condition that the structures are layered. Then the inverse Fourier transform is used to obtain the tomographic image.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 5A–5D show the 2D phantom used for the simulation, a reconstruction when sampled in a full 180 degree angular range, a reconstruction when sampled in a 120 degree angular range, and the Fourier transform space, respectively;

FIG. 6A shows the shape of the missing volume in the Fourier space when the maximum tilt angle is $\theta_{max}=60$ degrees, FIG. 6B shows volume sampled with a full rotation range of angle phi $\phi$ in a conical tilt scheme, and FIG. 6C shows reduced conical tilt volume;

FIG. 7 is a side plan cross-sectional view showing an implementation of a conical tilt sample motion system;

DETAILED DESCRIPTION OF THE PREFERRED EMBODIMENTS

When optimizing a tomographic x ray imaging system for resolution and throughput, a projection mode with a magnifying geometry is preferred since a coarse-resolution detector with nearly 100% efficiency can be used.

In this configuration, it is advantageous to place the sample as close to the source as possible. The flux to a pixel in the sample is $$F = B \cdot s^2 \cdot \left(\frac{\delta}{l_x}\right)^2,$$

where B is the brightness of the source and the $\delta$ is the pixel size in the sample. The brightness, when limited by the thermodynamic loading of the source is proportional to the inverse of the source size. Therefore, $$F \propto \frac{1}{s} s^2 \left(\frac{\delta}{l_s}\right)^2 = s\left(\frac{\delta}{l_s}\right)^2,$$

Using the projection mode at the resolution limit, $s \approx \delta$, then $$F \propto \frac{\delta^3}{l_s^2}.$$

For example, with a fixed geometry, if the resolution is relaxed by factor of 2, the source size and pixel size can both increase by a factor of 2, and the flux increases by a factor of 8. With a fixed resolution, if the sample distance is doubled, the flux is reduced by a factor of 4.

The following are some practical flux and exposure times that can be achieved with commercial components. With a micro-focused x-ray source, 2 Watts of electron excitation energy can be delivered to a 1 micrometer (μm) sized area. Assuming 50% absorption, and 1% conversion yield. The brightness from the source is $$B = \frac{2(W) \times 50\% \times 1\%}{(1 \ \mu m)^2 \times 4\pi (rad)^2}$$

$$\approx 10^{11} \gamma / (mm^2 \cdot mrad^2 \cdot sec.)$$

where γ is a 60 keV photon of Tungsten k-line emission. With a sample placed 1 millimeter (mm) away from the source, the flux incident on a 1 μm pixel is:

$$F = B \cdot s^2 \cdot \left(\frac{\delta}{l_s}\right)^2$$

$$= 10^{11} \gamma / (mm^2 \cdot mrad^2 \cdot sec.) \times 10^{-6} mm^2 \times 1 mrad^2$$

$$= 10^5 \gamma / sec.$$

If the resolution is fixed, the flux scales with the inverse square of the source-to-sample distance. For example, if this distance is increased to 10 mm, the flux on a 1 μm pixel is decreased by a factor of 100, to 1000 photons per second. With 1-second exposures, features with 0.3% and 3% contrast can be identified with 1 mm and 10 mm distance settings, respectively.

Figure 1:
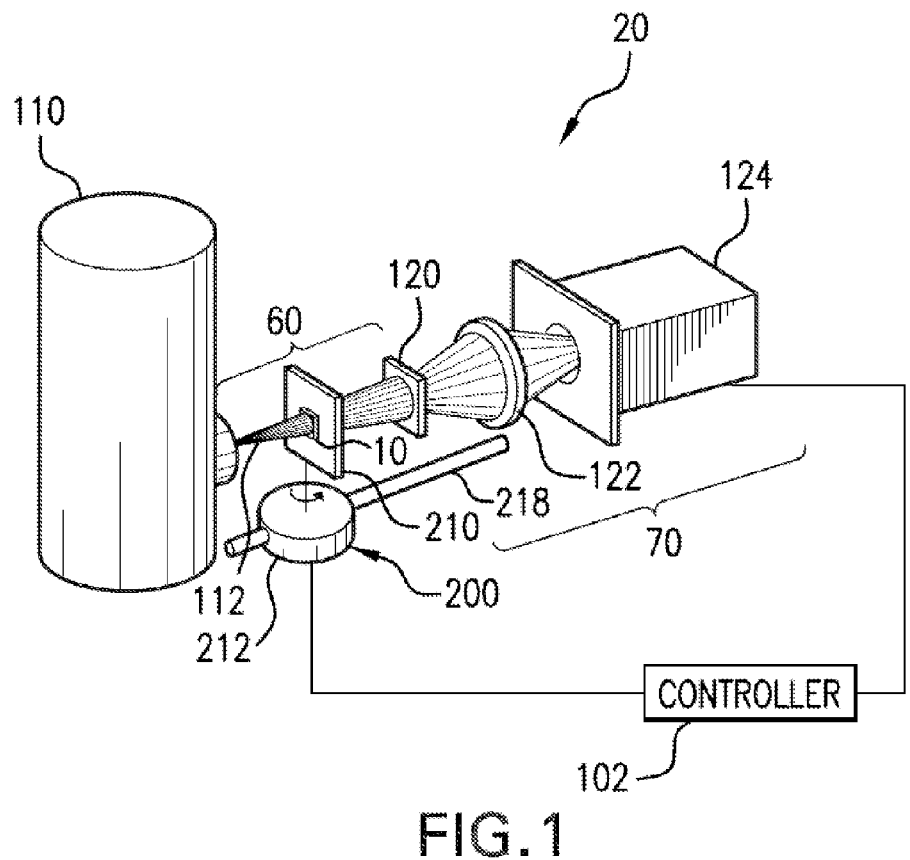
FIG. 1 is a schematic perspective view of an x ray imaging system according to the present invention.

FIG. 1 shows a projection x-ray imaging system 20 to which the present invention is applicable.

These systems typically comprise an x-ray source 110, a sample positioning and manipulations system 200, and a detector system 70.

The x-ray source 110 generates the x-ray beam 112, which is typically a diverging x-ray beam as is common in these x-ray projection systems that have no component, such as a zone plate lens, that focuses the x ray beam between the source 110 and a sample 10 and between the sample 10 and detector 70.

In one example, the x-ray source 110 is a rotating-anode type, with a tungsten target, but in other embodiments, the target comprises molybdenum, gold, platinum, silver, or copper.

The x-ray beam 112 is used to illuminate the sample 10. This is the sample 10 on which x-ray imaging is performed. In one example, the sample 10 is a packaged integrated circuit. In other examples, it is a biological sample. The x-ray imaging process allows for the non-destructive imaging of the internal features of this packaged integrated circuit in order to, for example, test the packaging process.

According to one aspect of the invention, a sample motion stage system 200 is provided in order to position the sample 10 in the x-ray beam 112 and move/rotate the sample in order to collect the images required for tomographic reconstruction of the sample's features or structures of interest. Specifically, in the illustrated embodiment, the sample 10 is held on a sample mount 210. This in turn projects from a mount base 212. This base 212 provides x,y,z translation and theta rotation.

In the preferred embodiment, an x-axis sample motion stage 218 is further provided. This x-axis sample motion stage 218 provides for relatively large or gross positioning of the sample 10 along the x-axis and in the x ray beam. This allows for the loading of the sample into the system 20 and the location of the sample 10 near to the x ray source 110, according to the present invention.

In another embodiment, the sample motion stage system 200 comprises at least two rotation stages, one (θ) stage with its axis perpendicular or substantially perpendicular to the x-ray beam axis 112, and the other (φ) stage, located on the (θ) stage, with its axis of rotation perpendicular to the plane of the sample 10, to perform conical tilt tomography data acquisition as described later herein, relative to FIG. 7.

In one embodiment, the magnification of the x ray section 60 is less than 10× to allow high resolution tomographic imaging of a relatively large sample.

The x ray section 60 of the imaging system 20 ends in a scintillation screen or scintillator 120. This converts the x-rays of the x-ray beam 112 into an optical signal. This optical signal is then received by the optical stage 70 for further magnification according to one embodiment and detection in a camera or film based image detector 124. Visible light coupling optics 122 is used to collect the light from the scintillator 120 and form an image on the image detector or camera 124.

Different materials can be used for the scintillator 120 such as Cesium Iodide (CsI) or Cadmium Tungstate ($CdWO_4$).

In one configuration, the thickness of scintillator 120 is between 10 μm and 1 millimeters (mm). The optical stage 70 then provides magnification of about 2 times.

In another implementation, thickness of scintillator 120 is between 10 μm and 500 μm, with the optical stage 70 providing a magnification of 5×.

In a still further implementation, a thinner scintillator 120 of between 5 μm and 250 μm is used with the optical stage 70 providing a magnification of 10×.

Also a thickness of 2 μm to 200 μm and an optical stage providing a magnification of 20× can be used. In still other examples, optical stage provides for magnification of about 50× or less.

By rotating the sample 10 using sample rotation stage 212 and collecting multiple images, tomography can be used to generate a 3D image. Applicable tomography algorithms include the filtered backprojection method. In others, the tomography algorithm is the algebraic reconstruction technique (generally abbreviated as ART) and it derivatives or the Fourier inversion technique.

Specifically, a controller 102 is provided to receive the image data from the camera 124 to create the images of the structures of interest from the sample 10. In a preferred embodiment, the controller 102 collects multiple images while controlling the sample motion stage system 200 to thereby control the rotation of the sample 10 in the x ray beam 112 and then perform tomographic reconstruction to create a three dimensional image of the sample's structures, while also controlling the x-axis stage 218 to ensure that the sample does not contact the source 110.

This imaging system 20 is used for imaging semiconductor chip packaging and associated components, in one application. It can also be used to image electronic circuit boards and micro-electro-mechanical system (MEMS) devices. Small animals and organic and geological samples can also be imaged.

Failures such as shorts and broken lines can often be observed with 2D real-time systems by directly imaging the suspected area or by tracking problematic lines identified from electrical testing. With some complex packaging types, 2D images often contain too many overlapping features for positive identification and 3D tomographic images are very valuable in providing a clear identification. Shorts in molding compounds caused by electro-migration or chemical reactions can often be imaged. This type of defect results when metal from the wire dissolves into the molding compound. They are often more difficult to see than direct wire contact shorts due to lower contrast, but can be effectively identified with x-ray techniques when combined with careful electrical testing.

Voids in solder bumps are usually visible by imaging with 2D real-time systems. To accurately determine the location, size, and distribution of voids, however, a 3D tomography system is invaluable. Wicking is difficult to identify from 2D images, but can be easily observed from virtual cross-sections of a 3D tomographic reconstruction.

Non-destructive x-ray imaging is an ideal tool for inspecting the contact surfaces to the die. Also, there can be small particles and clusters trapped in the substrate. They typically range from a few micrometers to tens of micrometers in size. Because of their small size, a high-resolution tool is required to image them, and since they often have very low contrast, they also tend to be very difficult to find from individual 2D images, which contain many overlapping features. The shorts represent such a case where the fault location was carefully determined from electrical testing and the copper particle was isolated between two bond wires. In more difficult cases where the particle is located between layers and among complex circuits, a 3D imaging system will be required to resolve the small particles in the depth direction. The operator must then carefully go through the 3D data set to find the particle.

Underfill entrapments typically result from particles being trapped in the solder bumps or other circuit structures. Since these particles usually have lower density than the solder material, they typically have a similar appearance as voids, but with irregular shapes. They can be observed with either 2D real-time or 3D tomographic imaging.

Most via delamination defects are very difficult to image with x-ray techniques because they typically occur under a solder bump with the crack parallel to the chip surface, hence the crack is blocked by the x-ray opaque solder and is only visible at extremely large tilt angles. However, by allowing full 180 degree sample tilt during tomographic data acquisition, x ray analysis is possible. Using high-tilt angle projections, it is usually possible to produce a high resolution 3D tomographic image that reveals the delamination crack. High resolution is essential since these cracks are often quite narrow, with a width of no more than a few micrometers at the widest point.

Figure 2:
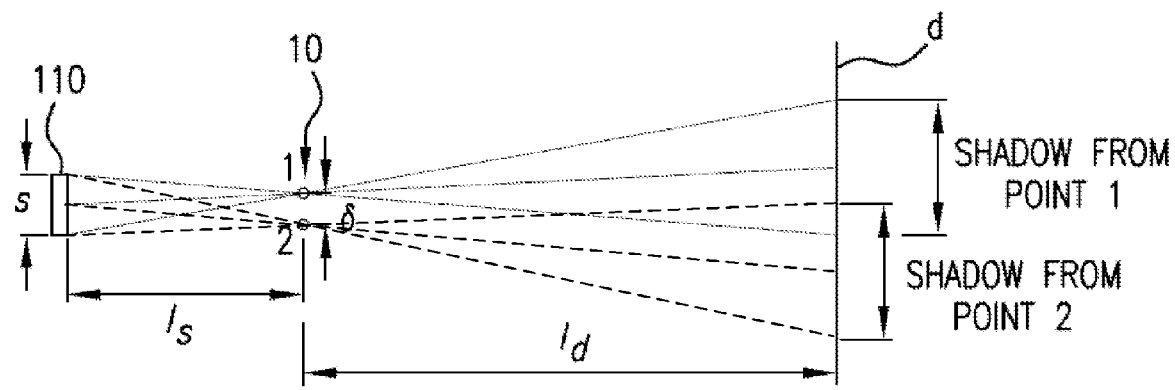
FIG. 2 is a schematic view showing the imaging characteristics of the system and the impact of source size on resolution.

The imaging properties of the system 20 are illustrated in FIG. 2 with an x-ray source having a lateral size s, two point objects 1 and 2, and a detector plane d. The separation between the source and the objects is $l_s$, and the separation between the object and the detector plane is $l_d$.

The magnification of this system is:

$$M = \frac{l_s + l_d}{l_s},$$

and the resolution limit determined by the imaging geometry is:

$$\delta \geq \max\left(\frac{M-1}{M}s, \frac{\delta_{det}}{M}\right).$$

Where $\delta_{det}$ is the detector resolution. A few extreme cases:

Proximity mode: $M \approx 1$, then $\delta = 0$. That is, infinitely high resolution can be achieved in proximity mode. In practice the system resolution is determined primarily by the detector resolution.

Projection mode: $l_d \gg l_s$, and $M \gg 1$, then $\delta \approx s$. In this mode, the system resolution is limited by the source size. If the detector can sample the image at sufficiently high resolution, the system resolution is approximately that of the source size. It should never be worse than the source size.

Figure 3:
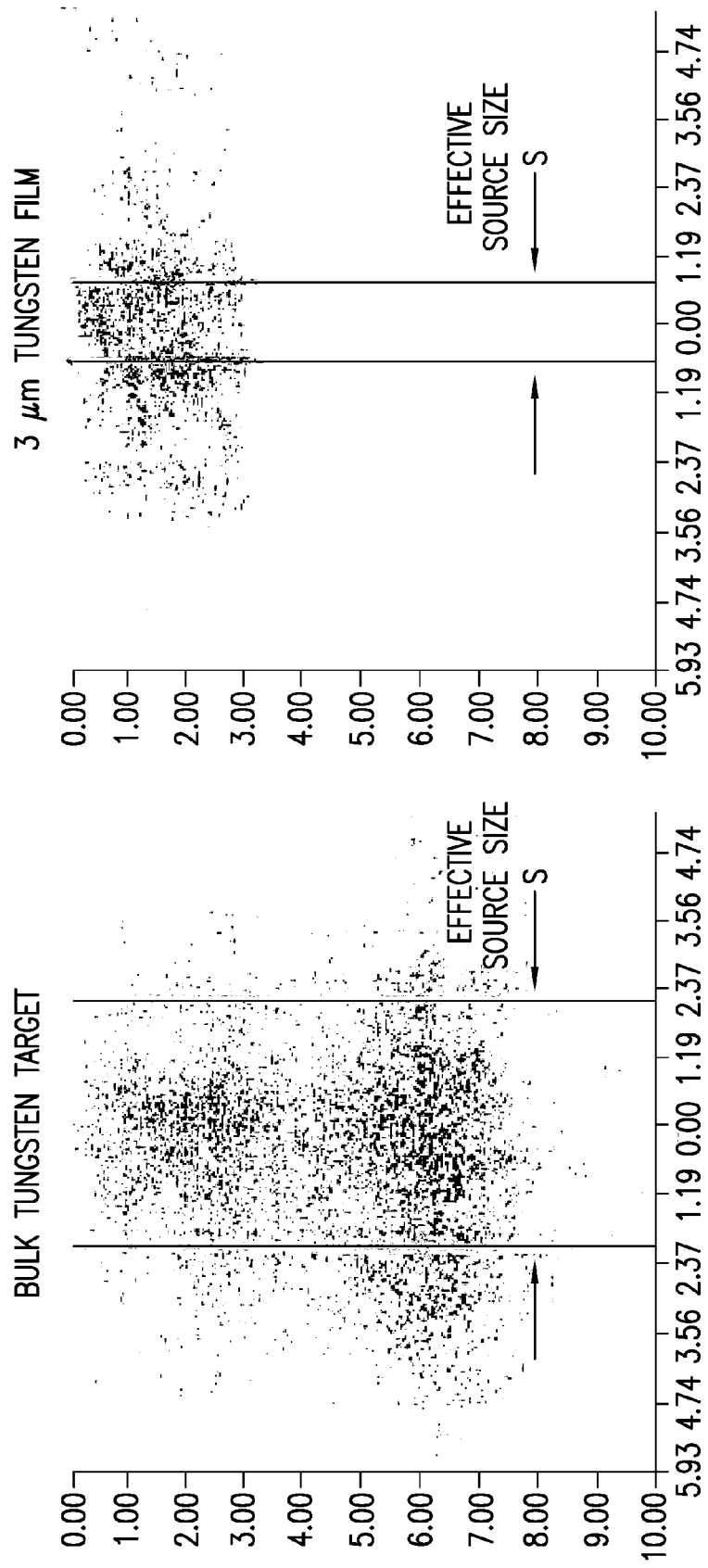
FIGS. 3A and 3B show Monte Carlo simulations of k-line x-ray generation sites inside a solid Tungsten target and a thin film Tungsten target, respectively.

FIGS. 3A and 3B show Monte Carlo simulations of k-line x-ray generation sites inside a solid Tungsten target and a thin film Tungsten target, respectively. The bombardment electron has 150 keV energy with infinitesimal size.

In the solid target, shown in FIG. 3A, the effective source size is about 5 µm. In contrast, with the film target, of FIG. 3B, the source size becomes 1 µm, but with about 50% of flux loss.

This illustrates that as limitations are place on source size in order to boost resolution, the system becomes increasingly photon starved. Thus, to compensate, the sample should be moved nearer the source 110 to boost flux when using these micro focused x ray sources with source sizes usually less than 5 µm and preferably less than 2 µm or about 1 µm or less.

Figure 4:
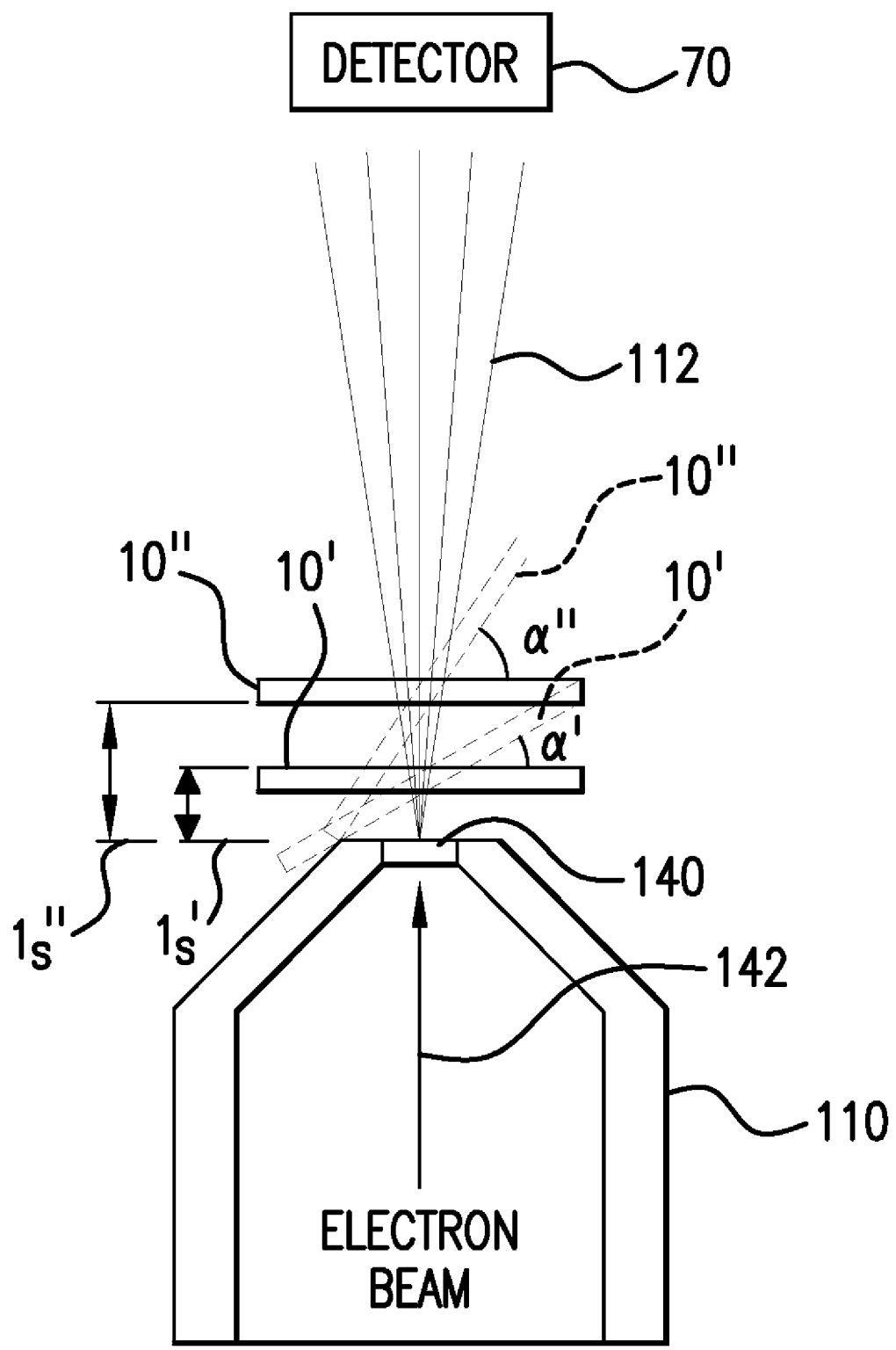
FIG. 4 is a side plan view illustrating the relationship between source-sample distance and tilt range limits.

FIG. 4 illustrates the effect on tilt range limit as the sample 10 is placed close to and far from the source 110.

To maximize the flux to sample 10, it is advantageous to place the sample 10 as close to the source 110, and specifically the source target 140, as possible. This criteria, however, has negative consequences for tomographic imaging since a large sample cannot be tilted to large angles without hitting the source 10.

Specifically, as illustrated in FIG. 4, the electron beam 142 of the source 110 strikes the target 140. This generates the x ray beam 112.

The sample 10 is located in this x ray beam 112 path. It must be rotated to image various structures within the sample. This rotation is also important when doing tomographic reconstruction of those structures.

As illustrated, the sample 10 can be located at two potential locations, 10', 10". These are located at increasing distances from the source 110, $l_{s'}$, and $l_{s''}$. As shown by the phantom lines 10' and 10", the sample can be tilted at a higher angle α" when the sample is at an increased distance from the source 110. Generally, the tilt angle α increases with increasing distance from the source by avoiding mechanical conflict with the source 110.

In one embodiment, $l_s$ is between 1 and 10 mm. It is usually between 1 and 4 mm, however.

FIGS. 5A–5D illustrate the effect of limited angle tomography. The 2D phantom used for the simulation is shown in FIG. 5A. It can be faithfully reconstructed when it can be sampled in full 180 degree angular range as illustrated in FIG. 5B. When the sample is rotated within only 120 degree range, part of the phantom outside the angular range shows poor quality as shown in FIG. 5C. The Fourier transform space, shown in FIG. 5D, provides a good understanding of this effect: the tomographic projection fills part of the Fourier space only along the angles sampled by the projections. The artifacts in the reconstruction result from the missing components in the Fourier space.

It is advantageous to fill as much Fourier space as possible. However, with the mechanical constraints of the projection system shown in FIG. 1, high resolution and throughput must be balanced against the tomographic image quality.

FIG. 6A shows the shape of the missing volume in the Fourier space. For example, if the maximum tilt angle is $\theta_{max} = 60$ degrees, then about 33% of the Fourier space is missing after the sample 10 is rotated through +/−60 degrees along an axis that is perpendicular to the direction of the beam 112.

One way to increase the sampling volume is to rotate the sample 10 in an additional axis to perform a conical tilt. For example as shown in FIG. 7, with a planar sample, the conical tilt is implemented by first tilting along an axis along the sample plane (θ) and an additional axis perpendicular to the sample plane phi (φ). The volume sampled with a full rotation range of angle phi φ is shown in FIG. 6B. The missing volume in this case is only about 13%.

A variation is based on the realization that most of the gain in the volume comes from two values for phi φ: 0 and 90 degree. Therefore a very efficient acquisition scheme is a reduced conical tilt in which phi φ takes two angles with 90 degree separation. The volume sampled with this scheme is shown in FIG. 6C and the missing volume is about 15%.

The mechanical system for this two angle reduced conical tilt scheme can be relatively easier to implement compared with a full conical system.

In one example, the sample motion stage comprises of at least two rotation stages, one (θ) stage 710 with its axis perpendicular or substantially perpendicular to the x-ray beam axis 112, and the other (φ) stage 712 with its axis perpendicular to the plane of the sample 10, to perform conical tilt tomography data acquisition.

The φ stage 712, with its axis perpendicular to the plane of the sample 10, has a restricted rotation range of 90 degrees, in one example, and is a goniometer. In another example the φ stage 712 positions the sample plane at two angles with 90 degree separation, for example, and is a goniometer with only 2 positions.

Preferably, the (θ) stage 710 is able to be rotated to as large angle as possible and φ stage 712 is rotated between −90 and +90 degrees.

In other examples, the (θ) stage 710 is able to be rotated only between −70 and +70 degrees.

Figure 8A:
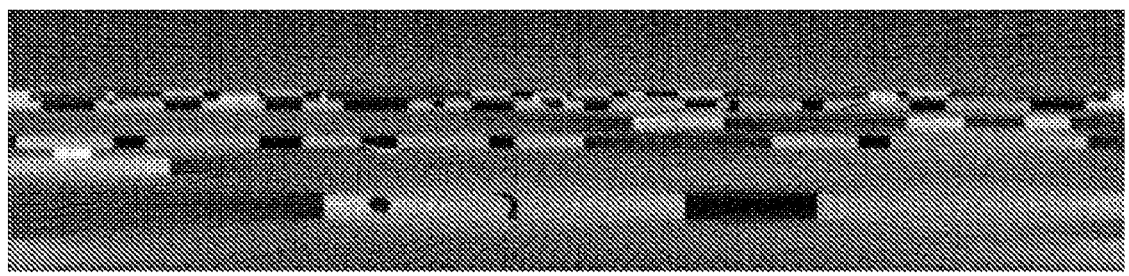
FIGS. 8A and 8B show a simulated reconstruction from tomographic data with an angular range between –60 and +60 degrees and a reconstruction with a priori knowledge injected to enforce layered structures.

For samples with layered structures such as semiconductor IC packaging, the missing values in the Fourier space causes a smearing effect such as shown in FIG. 8(*a*). For these structures, it is possible to use this a priori knowledge to fill-in the missing information so that a high-fidelity reconstruction can be obtained. This can be done in a couple of different ways:

In real space, we can force the structures to be layered by forcing the values between the layers to be the background value, and/or forcing the structures to be of square shaped in the case of integrated circuits and packaging samples.

Figure 8B:
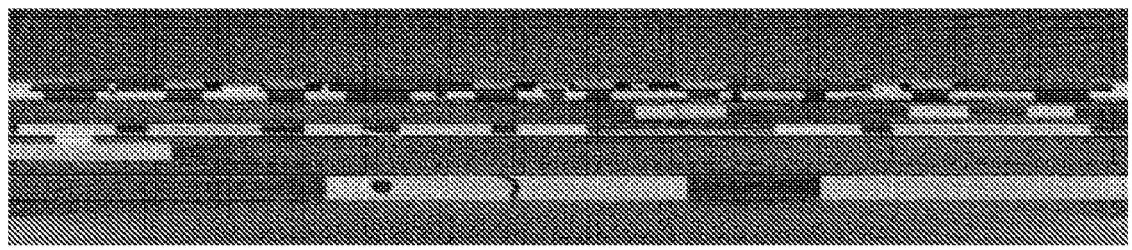

Alternatively, the computer aided design (CAD) data can be used to fill the information missing in the Fourier space. In cases the CAD design is not appropriate or available, a "guessed" model can be built from the reconstruction with the raw data with the help of the a priori knowledge. The model can then be used to fill the missing Fourier space. An example is shown is shown in FIG. 8B.

In Fourier space, the missing area can be interpolated by using the condition that the structures are layered and therefore the Fourier transform is periodic. An inverse Fourier transform can then be used to obtain the real structure.

For these layered structures, the most valuable projection angles are those with θ between −60 and +60 degrees, which define the planar circuit structure, and those with θ around 90 degree which define the layer structure. For these structures, it is efficient to acquire the low angle data between −60 and +60 degree with the sample placed very close the x-ray source, as shown in FIG. 4, 10', then increase the sample-to-source distance so that the sample can be tilted to 90 degrees to acquire the high-angle data. With this implementation, the conical tilt is not necessary. Generally, the source distance is between 1 and 10 mm at near position and between 10 and 50 mm at the far position.

When increasing the distance, the configuration is preferably modified to keep the geometric magnification constant. However, the geometric magnification can be varied but this leads to a need to mention modify the reconstruction.

Figure 9:
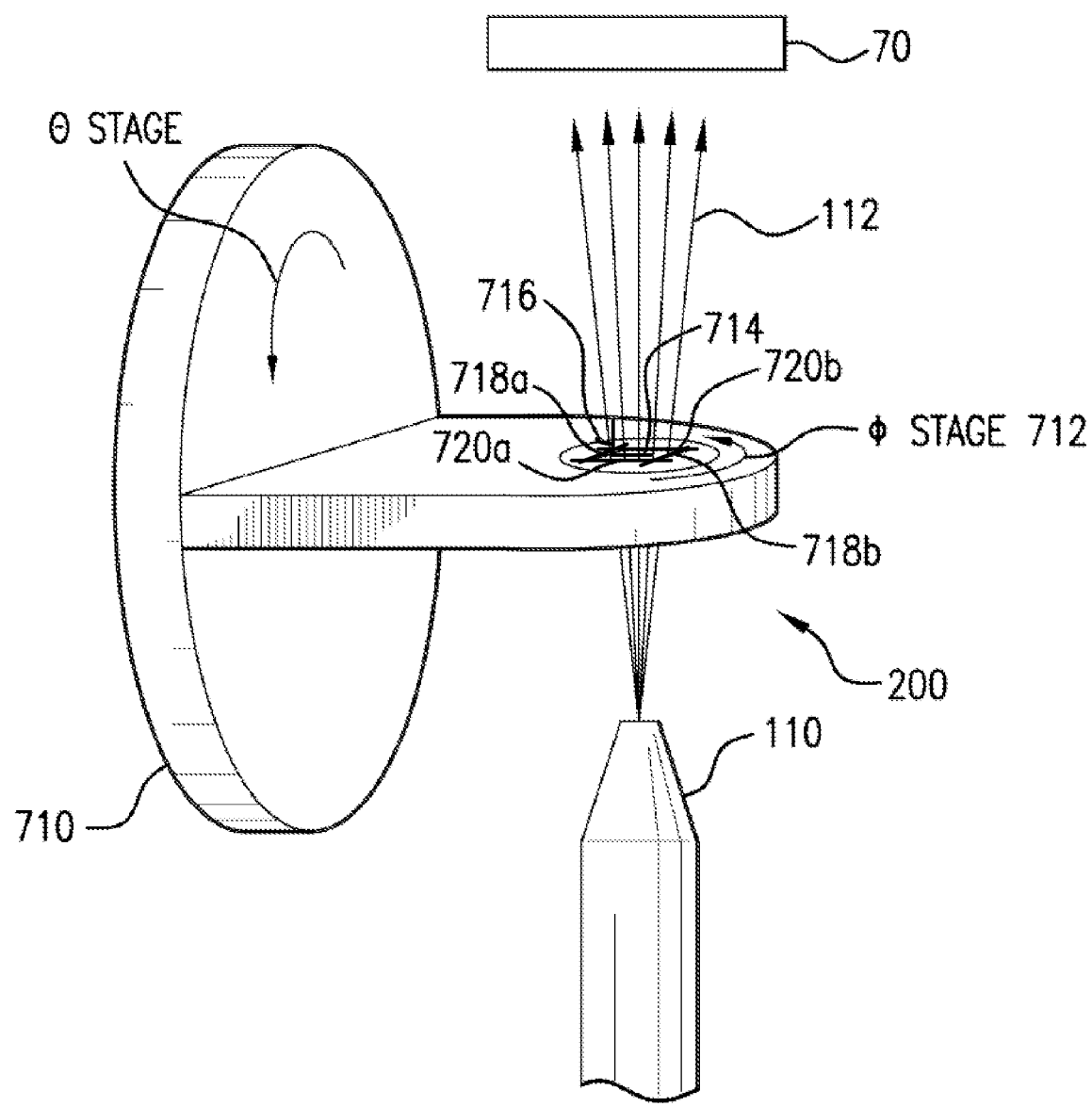
FIG. 9 is a schematic perspective view of a sample motion stage for performing the conical tilt sample motion.

FIG. 9 shows a schematic of one implementation of the sample motion stage 200 for tomographic imaging.

It comprises a θ stage 710 that has an axis of rotation that is perpendicular to the beam 112 to provide azimuthal or pitch rotation. The φ stage 712 has an axis of rotation that is perpendicular to a sample held on it to provide polar or roll rotation.

In one embodiment, an x,y,z aligment stage is carried on the φ stage 712. Specifically, a sample holder 714 is held on a y-axis rail 716 that projects parallel to the axis of rotation of the φ stage 712. The y-axis rail enables positioning along the y-axis. The y-axis rail is supported on two x-axis rails 720*a*, 720*b* that enable positioning in an axis of a plane of the sample. The x-axis rails 720*a*, 720*b* are in turn supported on z-axis rails 718*a*, 718*b* that enable positioning in the z-axis or other axis of the plane of the sample.

While this invention has been particularly shown and described with references to preferred embodiments thereof, it will be understood by those skilled in the art that various changes in form and details may be made therein without departing from the scope of the invention encompassed by the appended claims.

What is claimed is:

1. A projection x ray imaging system for imaging three dimensional structures, comprising:
   an x-ray source for generating an x ray beam;
   a sample motion stage system for rotating a sample around both polar (φ roll) and azimuthal (θ pitch) axes with respect to the x ray beam to enable tomographic data acquisition and comprising two rotation stages, with a φ stage located on a θ stage;
   a detector system for detecting the x ray beam after interaction with the sample; and
   a controller that receives image data of multiple images from the detector system taken while rotating the sample using the φ stage and the θ stage and performing tomographic reconstruction to create three dimensional images of the structures in the sample from the multiple images.

2. A projection x ray imaging system as claimed in claim 1, wherein the x-ray source is a micro-focused or nano-focused x-ray source.

3. A projection x ray imaging system as claimed in claim 1, wherein a source size of the x ray source is less than 50 μm.

4. A projection x ray imaging system as claimed in claim 1, wherein a source size of the x ray source is less than 5 μm.

5. A projection x ray imaging system as claimed in claim 1, wherein the θ stage has an axis of rotation that is perpendicular to the x-ray beam, and the φ stage has an axis of rotation that is perpendicular to a plane of the sample, to perform conical tilt tomography data acquisition.

6. A projection x ray imaging system as claimed in claim 5, wherein the φ-stage has a restricted rotation range of between −90 and +90 degrees.

7. A projection x ray imaging system as claimed in claim 5, wherein the φ-stage has a restricted rotation range of between −45 and +45 degrees.

8. A projection x ray imaging system as claimed in claim 5, wherein the θ stage has a restricted rotation range of between −70 and +70 degrees.

9. A projection x ray imaging system as claimed in claim 5, wherein the φ-stage comprises a goniometer.

10. A projection x ray imaging system as claimed in claim 5, wherein the φ-stage has only about two positions with about 90 degrees of separation.

11. A projection x ray imaging system as claimed in claim 1, wherein a distance between the sample and the source is between 1 and 10 millimeters (mm).

12. A projection x ray imaging system as claimed in claim 1, wherein a distance between the sample and the source is less than 2 mm.

13. A projection x ray imaging system as claimed in claim 1, further comprising:
   a sample holder for holding the sample; and
   an x, y, z alignment stage on the φ stage for carrying the sample holder, the x, y, z alignment stage enabling positioning of the sample on the φ stage.

14. A projection x ray imaging system as claimed in claim 13, wherein the x, y, z alignment stage comprises a first axis rail for positioning along a first axis and supporting the sample holder, a second axis rail for positioning along a second axis and supporting the first axis rail; and third axis rail for positioning along a third axis and supporting the second axis rail.

* * * * *